(12) United States Patent
Hyde

(10) Patent No.: US 11,786,683 B2
(45) Date of Patent: Oct. 17, 2023

(54) IRRIGATING INTRALUMINAL SUCTION INNER CANNULA SYSTEM

(71) Applicant: Blake J. Hyde, Fort Collins, CO (US)

(72) Inventor: Blake J. Hyde, Fort Collins, CO (US)

(*) Notice: Subject to any disclaimer, the term of this patent is extended or adjusted under 35 U.S.C. 154(b) by 0 days.

(21) Appl. No.: 17/643,816

(22) Filed: Dec. 10, 2021

(65) Prior Publication Data
US 2022/0184333 A1 Jun. 16, 2022

Related U.S. Application Data

(60) Provisional application No. 63/124,599, filed on Dec. 11, 2020.

(51) Int. Cl.
*A61M 16/00* (2006.01)
*A61M 16/04* (2006.01)
*A61M 16/20* (2006.01)

(52) U.S. Cl.
CPC .... *A61M 16/0463* (2013.01); *A61M 16/0003* (2014.02); *A61M 16/0051* (2013.01); *A61M 16/0434* (2013.01); *A61M 16/0465* (2013.01); *A61M 16/0475* (2014.02); *A61M 16/20* (2013.01); *A61M 2016/003* (2013.01); *A61M 2016/0027* (2013.01)

(58) Field of Classification Search
CPC .............. A61M 16/04; A61M 16/0475; A61M 16/0477; A61M 16/0402; A61M 16/0427; A61M 16/0051; A61M 16/0463; A61M 16/0003; A61M 16/0465; A61M 16/20
See application file for complete search history.

(56) References Cited

U.S. PATENT DOCUMENTS

| 3,788,326 A | * | 1/1974 | Jacobs | A61M 16/00 |
| | | | | 604/161 |
| 3,903,876 A | * | 9/1975 | Harris | A61M 16/0051 |
| | | | | 73/204.11 |
| 4,584,998 A | | 4/1986 | McGrail | |

(Continued)

FOREIGN PATENT DOCUMENTS

| WO | WO-03101516 A1 * | 12/2003 | A61M 16/04 |
| WO | WO-2011106754 A1 * | 9/2011 | A61M 16/0459 |

(Continued)

OTHER PUBLICATIONS

PCT Application No. PCT/US2021/062979, International Search Report and Written Opinion, dated Mar. 1, 2022, 12 pages.

*Primary Examiner* — Philip R Wiest
*Assistant Examiner* — Tyler A Raubenstraw
(74) *Attorney, Agent, or Firm* — Cozen O'Connor

(57) ABSTRACT

An irrigating intraluminal suction inner cannula system for a tracheostomy tube may be a suction-powered system that may be used for suction alone or a combination of rinse and intraluminal suction for tracheostomy tubes in place of conventional catheter-based intraluminal suction. An inner cannula includes chambers, or regions, and holes that facilitate intraluminal suction and cleaning at multiple locations within the tracheostomy tube. It may be applied/actuated by a patient, healthcare worker, caretaker, or via an electronic system either on-demand or on regular or triggered intervals, in either inpatient/hospital or outpatient/ambulatory care setting.

21 Claims, 10 Drawing Sheets

(56) References Cited

U.S. PATENT DOCUMENTS

| | | | |
|---|---|---|---|
| 4,627,433 A * | 12/1986 | Lieberman | A61M 16/0475 128/207.16 |
| 5,449,348 A | 9/1995 | Dryden | |
| 5,499,625 A * | 3/1996 | Frass | A61M 16/04 128/207.14 |
| 5,582,167 A | 12/1996 | Joseph | |
| 5,653,231 A | 8/1997 | Bell | |
| 5,735,271 A * | 4/1998 | Lorenzen | A61M 16/0833 128/207.14 |
| 5,819,723 A | 10/1998 | Joseph | |
| 6,135,111 A * | 10/2000 | Mongeon | A61M 16/0497 128/207.14 |
| 6,494,208 B1 * | 12/2002 | Morejon | A61M 1/83 128/207.14 |
| 6,725,862 B2 * | 4/2004 | Klinberg | A61M 16/0825 128/207.14 |
| 6,840,242 B1 | 1/2005 | McCoy | |
| 8,602,030 B2 | 12/2013 | Harrington et al. | |
| 8,808,226 B2 | 8/2014 | Deutsch | |
| 9,220,858 B2 * | 12/2015 | Nolan | A61M 16/06 |
| 9,463,297 B2 | 10/2016 | Fendler | |
| 10,016,575 B2 | 7/2018 | Vazales et al. | |
| 10,245,401 B2 | 4/2019 | Cuevas et al. | |
| 10,518,051 B2 | 12/2019 | Yavagal | |
| 10,799,092 B2 * | 10/2020 | Krimsky | A61B 1/00085 |
| 11,324,910 B2 * | 5/2022 | Wendling | A61M 39/02 |
| 2002/0014238 A1 | 2/2002 | Kotmel | |
| 2003/0084905 A1 * | 5/2003 | Ortiz | A61M 16/0475 128/207.29 |
| 2004/0079376 A1 | 4/2004 | Melker | |
| 2005/0205097 A1 * | 9/2005 | Kyle, Jr. | A61M 16/04 128/207.14 |
| 2007/0044807 A1 | 3/2007 | Madsen et al. | |
| 2008/0077036 A1 * | 3/2008 | Baker | A61B 5/087 600/532 |
| 2010/0186748 A1 * | 7/2010 | Morejon | A61M 16/042 128/207.14 |
| 2011/0144514 A1 * | 6/2011 | Booker | A61M 16/0475 128/207.14 |
| 2011/0190814 A1 * | 8/2011 | Mark | A61B 10/02 606/176 |
| 2012/0136277 A1 * | 5/2012 | Landrigan | A61B 10/025 600/566 |
| 2012/0180796 A1 * | 7/2012 | Bateman | A61M 16/0427 128/207.14 |
| 2012/0247473 A1 * | 10/2012 | Fendler | A61M 16/0479 128/205.27 |
| 2013/0255692 A1 * | 10/2013 | McBurney | A61M 16/0465 128/207.14 |
| 2014/0144432 A1 * | 5/2014 | Avitsian | A61M 16/042 128/202.16 |
| 2014/0150782 A1 * | 6/2014 | Vazales | A61M 25/1018 128/202.16 |
| 2014/0216449 A1 * | 8/2014 | Chang | A61M 16/0409 128/202.16 |
| 2014/0277066 A1 * | 9/2014 | Schaeffer | A61M 16/0427 606/192 |
| 2014/0360508 A1 * | 12/2014 | Coates | A61M 16/0475 128/207.14 |
| 2015/0011828 A1 * | 1/2015 | Vilasi | A61M 16/0816 600/116 |
| 2015/0018710 A1 * | 1/2015 | Furlong | A61B 1/00133 600/563 |
| 2015/0136123 A1 * | 5/2015 | Donlon | A61M 16/0497 128/200.26 |
| 2015/0209535 A1 * | 7/2015 | Cole | A61M 16/04 128/202.16 |
| 2015/0258297 A1 * | 9/2015 | Blom | A61M 16/0427 128/200.26 |
| 2015/0265790 A1 * | 9/2015 | Nolan | A61M 16/0486 128/202.16 |
| 2016/0029923 A1 * | 2/2016 | Ozenne | A61M 16/0461 600/473 |
| 2016/0158111 A1 * | 6/2016 | Besser | A61M 16/04 604/35 |
| 2016/0199608 A1 * | 7/2016 | Morejon | A61M 16/0463 128/204.18 |
| 2017/0007295 A1 * | 1/2017 | Geisz | A61B 17/3421 |
| 2017/0100557 A1 * | 4/2017 | Worley | A61M 16/0465 |
| 2017/0143922 A1 * | 5/2017 | Chang | A61M 16/0459 |
| 2017/0209022 A1 * | 7/2017 | Molnar | A61B 1/303 |
| 2017/0319804 A1 * | 11/2017 | Elia | A61M 16/0402 |
| 2017/0368283 A1 * | 12/2017 | Suijs | A61M 16/04 |
| 2018/0093059 A1 * | 4/2018 | Ozenne | A61M 16/0475 |
| 2018/0126106 A1 * | 5/2018 | Guan | A61M 16/0434 |
| 2018/0272081 A1 * | 9/2018 | Porter | A61M 16/0488 |
| 2018/0296782 A1 * | 10/2018 | Chapiro | A61M 16/044 |
| 2018/0318543 A1 * | 11/2018 | Coleman | A61M 16/0463 |
| 2019/0060594 A1 * | 2/2019 | Qiu | A61M 16/0486 |
| 2019/0192811 A1 * | 6/2019 | Wei | A61B 1/05 |
| 2019/0217033 A1 * | 7/2019 | Suijs | A61M 16/0486 |
| 2019/0336714 A1 * | 11/2019 | Vazales | A61M 16/0484 |
| 2020/0009340 A1 * | 1/2020 | Elia | A61M 16/201 |
| 2020/0038046 A1 * | 2/2020 | Schwamb | A61B 90/98 |
| 2020/0113427 A1 * | 4/2020 | Molnar | A61M 16/0402 |
| 2020/0337547 A1 * | 10/2020 | Molnar | A61B 1/0014 |
| 2021/0093814 A1 * | 4/2021 | Nolan | A61M 16/0463 |
| 2021/0146073 A1 * | 5/2021 | Owens | A61M 16/0465 |
| 2021/0187228 A1 * | 6/2021 | Musuku | A61M 16/0459 |
| 2021/0220591 A1 * | 7/2021 | Garrett | A61M 16/0475 |
| 2021/0393907 A1 * | 12/2021 | Ahmed | A61M 16/0463 |
| 2022/0062574 A1 * | 3/2022 | Tassitano | A61M 16/0003 |

FOREIGN PATENT DOCUMENTS

| | | | |
|---|---|---|---|
| WO | 2014088904 A1 | | 6/2014 |
| WO | WO-2021209734 A1 * | | 10/2021 |
| WO | WO-2022018394 A1 * | | 1/2022 |

* cited by examiner

FIG. 1C  FIG. 1D

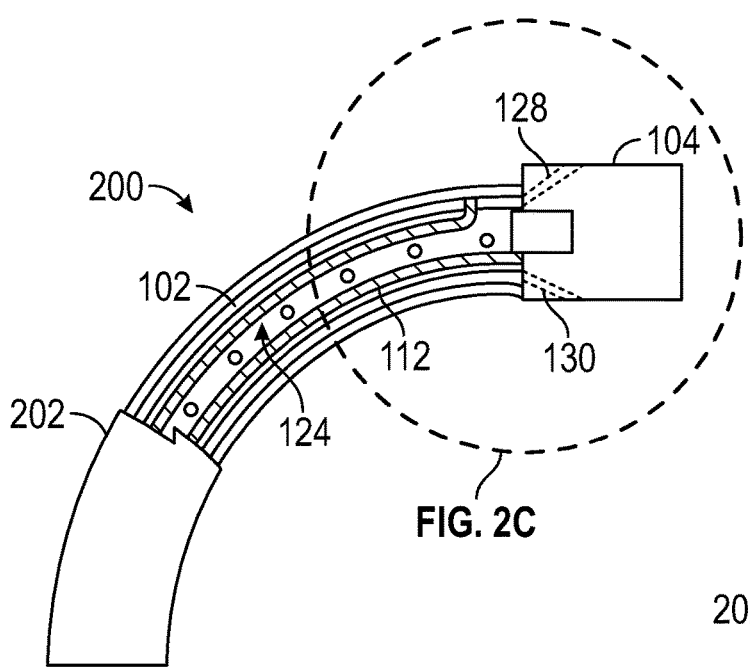
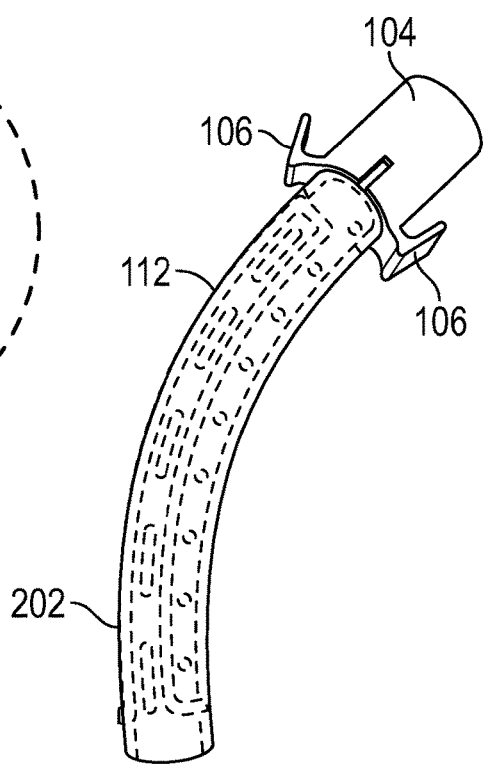
FIG. 2A
FIG. 2B
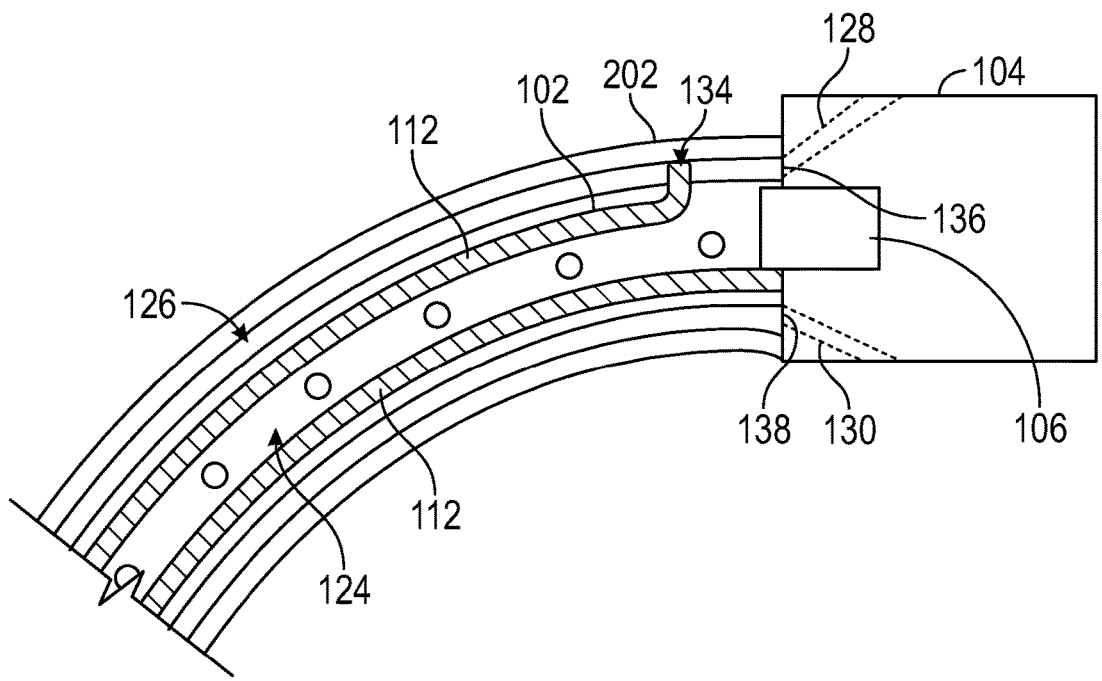
FIG. 2C

500

502
Insert inner cannula into tracheostomy tube and secure with clips.

504
Attach suction, or suction and irrigant lines to cannula.

506
Attach suction, or suction and irrigant lines to vacuum and irrigant sources through an actuating device.

508
Use actuating device to perform suction alone, or suction with Irrigation.

FIG. 5

IRRIGATING INTRALUMINAL SUCTION INNER CANNULA SYSTEM

CROSS-REFERENCE TO RELATED APPLICATIONS

This application claims priority to Provisional Patent Application Ser. No. 63/124,599 filed Dec. 11, 2020, which is hereby incorporated by reference in its entirety.

BACKGROUND

Intubation refers to the placement of an endotracheal breathing tube into a patient's airway, terminating in the trachea. The breathing tube may be inserted orally, nasally, or via tracheostomy—an insertion route through the skin and soft tissues of the neck—through and ultimately terminating within the trachea. These measures are taken to either temporarily or permanently support breathing or ventilation. Risks and problems associated with placement, use, and care of an endotracheal breathing tube range from discomfort and inconvenience to serious medical risks and poor health outcomes.

Tracheostomy tube care requires regular evacuation of secretions from within the innermost lumen of the tube (i.e., "intraluminal") for safe use and comfort. In some situations, evacuation may need to be performed as frequently as every 30 minutes. Even when not sedated, few patients are able to perform effective, safe, regular catheter-based intraluminal suctioning without assistance, thus rendering them dependent upon others to perform this vital task, often leading to depression, anxiety, and agitation. Even with assistance, patients frequently experience discomfort during suctioning procedures. The reasons for this are two-fold: first, frequent misuse of suction catheter (i.e., suction catheter is applied too deep/proximal within the airway); and second, patient's inability to time application of suction (negative pressure) during their breath cycle, leading to "surprise" suctioning and its resultant breathlessness sensation, change in airway pressures, and elicitation of cough reflex.

FIGS. 7A-7C illustrate various aspects of relevant basic anatomy of endotracheal tubes, and prior art tracheostomy tube features. FIG. 7A is a cross-sectional side view diagram of patient 700 showing various types of endotracheal tubes. FIG. 7B is a perspective view of a tracheostomy tube with an inner cannula, and FIG. 7C is a perspective view of a fenestrated tracheostomy tube and inner cannula. FIGS. 7A-7C are best viewed together in the following discussion.

A patient 700 has a trachea 702 that is part of the airway to the lungs (not shown) of patient 700. To support breathing, patient 700 may be intubated in several ways that are illustrated in FIG. 7A. Intubation may be achieved by a longer nasotracheal tube via path 704 inserted through the nasal passages, past vocal cords 710, and into trachea 702. Alternatively, a similar length oral endotracheal tube via path 706 may be inserted through the oral cavity and into trachea 702. Further, a shorter tracheostomy tube 708 may be inserted directly into trachea 702 through a surgical tracheostomy, region 712.

During positive pressure or mechanical ventilation, an inflatable cuff 714 surrounding tracheostomy tube 708 may be inflated via cuff inflation valve 716, external monitoring balloon 718, and associated tubing 720 to provide a seal between tracheostomy tube 708 and trachea 702 to prevent air leak around the tube. This is referred to as a "cuffed" tube. Cuff 714 may be either inflated or deflated, depending on the needs of patient 700. A comparable tube without such a cuff is referred to as an "uncuffed" tube as shown, for example, in FIG. 7C.

As shown in FIG. 7B, tracheostomy tube 708 includes a flange 722 which is placed against the neck of patient 700 to maintain tracheostomy tube 708 in the correct position and provide certain functionality. A removable inner cannula 724 is an additional feature of some prior art tracheostomy tubes, and may be incorporated with either cuffed or uncuffed tracheostomy tubes. Air is exchanged with patient 700 through hub 726 via the innermost lumen of tracheostomy tube 708 (or inner aspect, or lumen, of the inner cannula 724, if present). Hub 726 of inner cannula 724 includes clips 728 that engage with clip attachments 730 on flange 722.

FIG. 7C illustrates principles of a fenestrated tracheostomy tube. A fenestration 732 is included in tracheostomy tube 708 above a region 734 where an inflatable cuff would be located. A corresponding fenestration 736 may be included in inner cannula 724, if used. Fenestrations 732 and 736 permit airflow, which allows patient 700 to speak and cough more effectively. The methodologies, concepts, and designs, herein applied to and described using tracheostomy tubes, may also be applied to nasotracheal tubes and oral endotracheal tubes.

Most prior art secretion management processes use only suction to clear secretions from a tracheostomy tube. At present, there is no manner to safely rinse the inner lumen of a tracheostomy tube to prevent build-up of secretions, clogging, and acute loss of airway. As a result, the patient may be subjected to more advanced intervention or additional procedures due to inadequate clearing of the tracheostomy tube.

Prior art intraluminal tracheostomy secretion clearance through manual suction-based catheters may also introduce risk of infection to the patient and frequently causes airway trauma. It can also cause significant patient and caretaker psychosocial distress, displaced patient autonomy, taxed healthcare personnel resources, and burdened caretakers, all of whom may be exposed to airborne pathogens from the patient's airway. Such secretion clearance also needs to be performed frequently, thus further taxing healthcare personnel and/or caretaker time and resources as well as making the patient passive in their own care.

Presently available tracheostomy tubes that incorporate irrigation and/or suction functions do so at a single site within the airway (i.e., subglottic/"above the cuff", or proximal tip) and most commonly, not within the lumen of the tube. Those that evacuate the lumen of the tube do not address the distal tip or the extraluminal sections, and furthermore, do so without irrigation, thus making them prone to imminent airway loss from clogging. None of these devices have gained widespread acceptance in clinical use, and thus, clogging/airway loss, infection, and the burdens of standard, manual, catheter-based intraluminal suction systems remain the mainstay of tracheostomy tube care. Additionally, failure or clogging of these designs typically requires removal of the entire tracheostomy tube to cure, which can be dangerous.

SUMMARY

An irrigating intraluminal suction inner cannula system for a tracheostomy tube may be a suction-powered system that may be used for suction alone or a combination of rinse and intraluminal suction for tracheostomy tubes in place of conventional catheter-based intraluminal suction. An inner cannula includes chambers, or regions, and holes that facilitate intraluminal suction and cleaning at multiple locations within the tracheostomy tube. It may be applied/actuated by a patient, healthcare worker, caretaker, or via an electronic system either on-demand or on regular or triggered intervals, in either inpatient/hospital or outpatient/ambulatory care setting.

In a first aspect, an inner cannula for use with a tracheostomy tube includes a first tube having a first diameter for insertion in the tracheostomy tube, said first tube further comprising a plurality of holes between an intraluminal space of the first tube and an outer surface of the first tube, and one or more ridges on the outer surface of the first tube that divide an airspace surrounding the outer surface into a plurality of regions; and a second tube fused to a distal end of the first tube and having a second diameter larger than the first diameter, the second tube comprising a first passage between an outer surface of the second tube and a first region of the plurality of regions and a second passage between an outer surface of the second tube and a second region of the plurality of regions.

In a second aspect, an irrigating intraluminal suction inner cannula system includes an outer tracheostomy tube and an inner cannula positioned inside the outer tracheostomy tube. The inner cannula includes a first tube having a first diameter for insertion in the outer tracheostomy tube, said first tube further comprising a plurality of holes between an intraluminal space of the first tube and an outer surface of the first tube, and one or more ridges on the outer surface that divide an airspace between the outer surface of the inner cannula and an inner surface of the outer tracheostomy tube into a plurality of regions; and a second tube fused to a distal end of the first tube and having a second diameter larger than the first diameter, the second tube comprising a first passage between an outer surface of the second tube and a first region of the plurality of regions and a second passage between the outer surface of the second tube and a second region of the plurality of regions. The system also includes an irrigant line attached to the first passage in the second tube and in communication with the first region a suction line attached to the second passage in the second tube and in communication with the second region; and an actuating device coupled between the irrigant line and a source of irrigant and coupled between the suction line and a vacuum source, said actuating device controllably connecting the irrigant line to the source of irrigant and the suction line to the vacuum source.

In a third aspect, an irrigating intraluminal suction and extraluminal suction inner cannula system includes an outer tracheostomy tube comprising one or more openings along its length and an inner cannula positioned inside the outer tracheostomy tube, the inner cannula includes a first tube having a length and diameter for insertion in the outer tracheostomy tube, said first tube further comprising a plurality of openings between an intraluminal space of the first tube and an outer surface of the first tube, a first ridge dividing the outer surface of the first tube into an irrigation region and a first suction region, and a second ridge creating a second suction region on the outer surface of the first tube; and a second tube fused to a distal end of the first tube and having a diameter larger than the first tube. The system also including an irrigant line attached to an irrigant passage in the second tube and in communication with an airspace formed between the outer surface of the first tube and an inner surface of the outer tracheostomy tube in the irrigation region; a first suction line attached to a first suction passage in the second tube and in communication with an airspace formed between the outer surface of the first tube and an inner surface of the outer tracheostomy tube in the first suction region; a second suction line attached to a second suction passage in the second tube and in communication with an airspace formed between the outer surface of the first tube an inner surface of the outer tracheostomy tube in the second suction region; and an actuating device coupled between the irrigant line and a source of irrigant and coupled between the first and second suction lines and a vacuum source, said actuating device controllably connecting the irrigant line to the source of irrigant and the first and second suction lines to the vacuum source.

In another aspect, a method of cleansing a tracheostomy tube having an outer tracheostomy tube and an inner cannula comprising a plurality of holes and one or more ridges dividing an airspace between the outer tracheostomy tube and the inner cannula into a plurality of regions when the inner cannula is inserted in the outer tracheostomy tube, includes attaching a suction line to the inner cannula so that it is in communication with a first region of the plurality of regions; attaching an actuating device between the suction line and a vacuum source, said actuating device controllably connecting the suction line to the vacuum source; and controlling the actuating device to suction from a lumen of the inner canula through a first portion of the plurality of holes, the first region and the suction line.

Further, the method may include attaching an irrigant line to the inner cannula so that it is in communication with a second region of the plurality of regions; attaching the actuating device between the irrigant line and a source of irrigant, said actuating device controllably connecting the irrigant line to the source of irrigant; and controlling the actuating device to provide irrigant to the lumen of the inner canula through a second portion of the plurality of holes, the second region and the irrigant line.

Use of the irrigating intraluminal suction inner cannula system does not preclude the use of present standard catheter-based intraluminal suctioning, if needed or desired. The use of the irrigating intraluminal suction inner cannula system also does not limit the use of existing subglottic extraluminal (e.g., subglottic) suctioning systems, and may also incorporate these designs.

In the event of suboptimal performance of the irrigating intraluminal suction inner cannula system, the inner cannula may be removed and replaced without removing the tracheostomy tube. Lastly, in certain situations (e.g., when attached to mechanical ventilation, or when using a filter or other such cap externally to limit secretions) the irrigating intraluminal suction inner cannula system achieves both irrigation and suction within a "closed system," thus reducing or eliminating potentially infectious aerosols and/or particulates that result from existing "open" type catheter-based tracheostomy suctioning, and thereby reducing the risk to health care workers and caretakers to respiratory-borne pathogens.

Embodiments of the irrigating intraluminal suction inner cannula system disclosed herein address these concerns via its novel design and use in a closed system, as described hereinbelow. For example, by creating separate chambers for suction and irrigation within the tracheostomy tube—the irrigating intraluminal suction inner cannula system achieves intraluminal tracheostomy suction and irrigation in a way that is presently unavailable. As a result, the shortcomings and risks of prior art technology are avoided.

BRIEF DESCRIPTION OF THE DRAWINGS

FIG. 1C is a top view of the cannula of FIG. 1A.

FIG. 1D is a bottom view of the cannula of FIG. 1A.

FIG. 2A is a cutaway side view of an irrigating intraluminal suction cannula with an outer lumen, in embodiments.

FIG. 2B is an oblique view of the cannula system of FIG. 2A.

FIG. 2C is an expanded view of a portion of the cannula system of FIG. 2A.

FIG. 5 is a flowchart illustrating a method of using an irrigating intraluminal suction inner cannula system.

DETAILED DESCRIPTION

The principles according to the present disclosure may have particular application in a tracheostomy tube, and thus will be described below chiefly in this context. It is also understood, however, that principles and aspects according to the present disclosure may be applicable to oral endotracheal or nasotracheal tubes, or other irrigating suction catheters used in healthcare or industry.

In the discussion above and to follow, the term "proximal" is used to indicate closer toward the lung of a patient and/or toward the lung-side tip of a tracheostomy tube. The term "distal" is used to indicate farther away from a patient and/or toward the equipment outside the patient or the external end of the tracheostomy tube. Other terms used herein may be defined as follows:

Cannula—A tube that is inserted into a body cavity, duct, or vessel.

Lumen—The space inside a cannula.

Intraluminal—Within the innermost lumen, between the ends of the cannula.

Extraluminal—Outside the cannula or at either or both ends of the cannula. As used herein, extraluminal applies to the outer most tube in any context, or at either end of a tube or cannula.

Subglottic—Generally, situated below the glottis. As used herein, subglottic indicates an extraluminal region of a trachea that is above an inflatable cuff of a tracheal tube and below the vocal cords.

The innermost airway lumen of an endotracheal tube, including tracheostomy tubes, ranges in inner diameter from 2 mm in neonatal tubes, and up to approximately 14 mm inner diameter in adults, with the lower range being limited by effective airflow/ventilation to and from the patient's airway. The upper range of size is impacted by the outer diameter of an endotracheal tube or tracheostomy tube, and its ability to fit in the airway—specifically, beyond the vocal cords/glottis and into the trachea—generally limited in size to no larger than approximately 15 mm.

An irrigating intraluminal suction inner cannula system as discussed herein generally includes a tracheostomy tube and inner cannula. The inner cannula is inserted within the tracheostomy tube and provides both suction and irrigation of the tracheostomy tube. FIGS. 1A-1D depict inner cannula 100, in an embodiment, while FIGS. 2A-2C depict inner cannula 100 in combination with a tracheostomy tube to form an irrigating intraluminal suction inner cannula system 200, in embodiments.

Figure 1A:
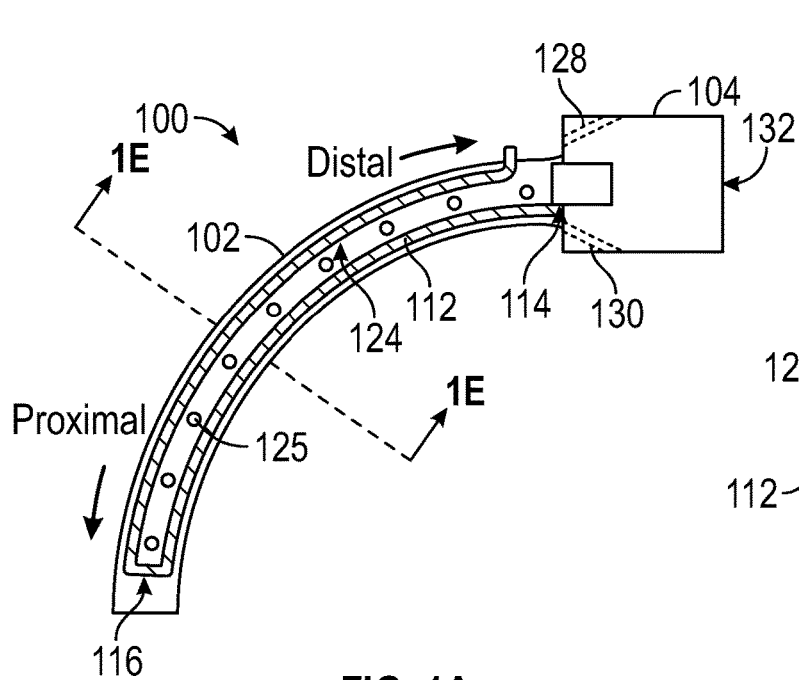
FIG. 1A is a side view of an irrigating intraluminal suction inner cannula, in embodiments.
Figure 1B:
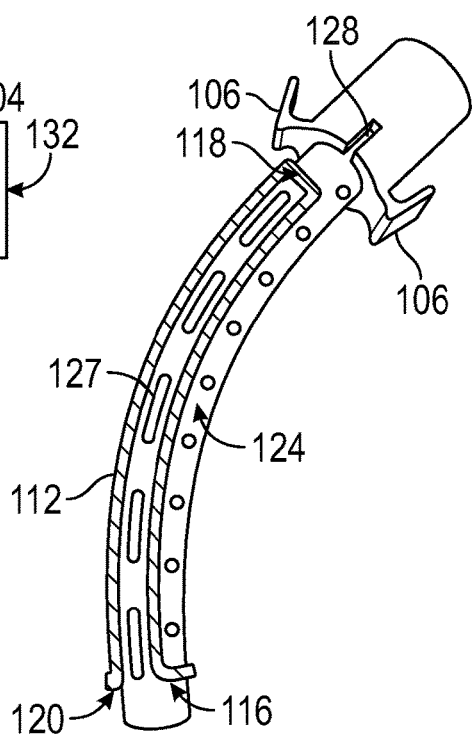
FIG. 1B is an oblique view of the cannula of FIG. 1A.
Figure 1E:
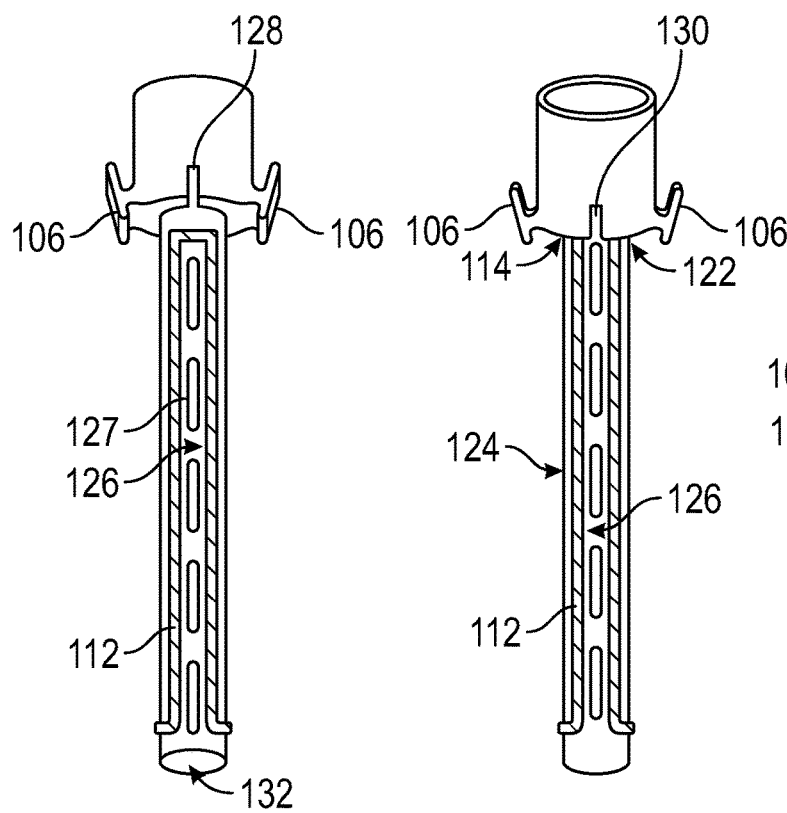
FIG. 1E is a cross-sectional view of the inner cannula of FIG. 1A.
Figure 1E:
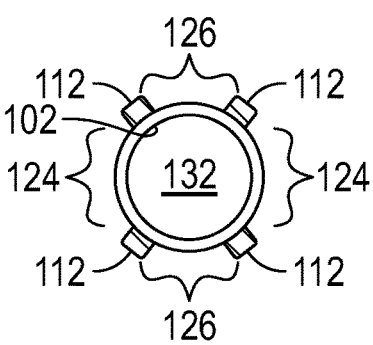

FIG. 1A shows a side view of inner cannula 100 with intraluminal suction and irrigation, in embodiments. FIGS. 1B, 1C and 1D show oblique, top, and bottom views of inner cannula 100, respectively. FIG. 1E is a cross-sectional view of FIG. 1A at line 1E-1E. FIGS. 1A-1E are best viewed together in the following description.

Inner cannula 100 includes a single curved semi-rigid plastic first tube 102 fused to rigid plastic second tube 104. Inner cannula 100 may fit into a patient's existing tracheostomy tube 202 (as shown in FIGS. 2A-2D) or into a tracheostomy tube specifically designed for use with inner cannula 100. The outer tracheostomy tube 202 may or may not be equipped with a balloon cuff (such as cuff 604 of FIG. 6) for use with positive pressure ventilation (i.e., "cuffed" or "uncuffed" tracheostomy tubes) known in prior art. Inner cannula 100 may be secured with appropriate retaining clips 106 for patient's native tracheostomy tube 202 or accompanying specifically designed tracheostomy tube. Inner cannula 100 may have a variety of diameters, thicknesses and lengths depending on the needs of the patient or its use in an endotracheal tube, for example. In embodiments, semi-rigid plastic first tube 102 has a smaller diameter than rigid plastic second tube 104. Intraluminal space 132 is formed throughout the interior of inner cannula 100.

Inner cannula 100 includes a continuous elevated ridge 112 on an outer surface of first tube 102, in a specific arrangement and height as to abut the inner lumen of a rigid outer tracheostomy tube 202. Ridge 112 divides the outer surface of first tube 102 into several regions 124, 126, or chambers. Starting from point 114 where first tube 102 is fused to second tube 104, ridge 112 extends along the length of first tube 102 in the proximal direction, around the circumference of first tube 102 at point 116, then back along first tube 102 in the distal direction. Before reaching second tube 104, ridge 112 again goes around the circumference of first tube 102 at point 118, extends in the proximal direction to point 120 then back up first tube 102 to culminate at point 122 where first tube 102 is fused to second tube 104.

The regions 124, 126 of first tube 102 formed by ridge 112 each contain a series of openings between the outer surface and intraluminal space 132 to allow for the movement of air and/or fluid. Region 124 includes holes 125 and is located on either side of first tube 102 while region 126 includes slots 127 and is located on the top and bottom of first tube 102.

Although holes and slots are shown, this is for purposes of illustration. In embodiments, the locations of holes and slots may be reversed. In addition, all of the openings may be slots, or all may be holes, or holes 125 and 127 may be of varying sizes or other shapes to facilitate function. Similarly, the shapes and orientations of the ridges are shown in FIGS. 1A-1E for purposes of illustration only and may be configured differently to facilitate the functions described herein.

In embodiments, the rigid plastic second tube 104 includes first passage 128 and second passage 130 positioned 90 degrees from retaining clips 106, although other locations are contemplated as long as first and second passages 128 and 130 connect to regions 124 and 126, respectively. First and second passages 128 and 130 may be slots or enclosed passages through second tube 104. First passage 128 extends at an angle from an upper external surface of second tube 104 to an opening in the proximal end of second tube 104 adjacent to first tube 102. In embodiments, first passage 128 communicates with the airspace created by ridge 112 between first tube 102 and an abutting inner surface of an outer tracheostomy tube 202 in region 124. Holes 125 communicate between the airspace of region 124 and intraluminal space 132. In a similar way, second passage 130 extends at an angle from a lower external surface of second tube 104 opposite of first passage 128 to an opening in the proximal end of second tube 104 adjacent to first tube 102 but opposite from the opening of first passage 128. In embodiments, second passage 130 also communicates with an airspace created between ridge 112 between first tube 102 and an abutting inner surface of an outer tracheostomy tube 202 but in region 126 instead of region 124. Region 126 includes slots 127, which also communicate between the airspace of region 126 and intraluminal space 132.

Figure 3:
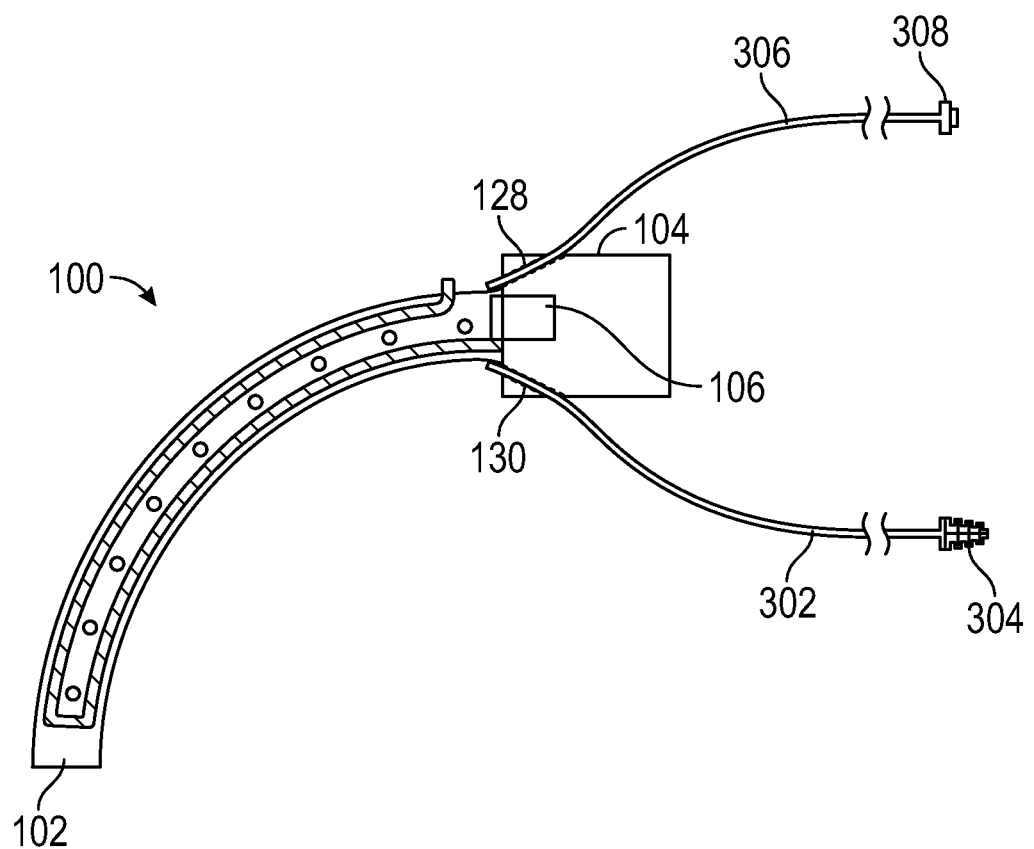
FIG. 3 is a side view of a cannula with irrigant and suction connections, in embodiments.

As discussed in more detail in connection with FIG. 3, flexible plastic tubing having a varying diameter, thickness, and length may be connected to first passage 128 on the upper surface of second tube 104. As further discussed below, flexible plastic tubing having a varying diameter, thickness, and length may be connected to second passage 130 on the lower surface of second tube 104. References to upper surface and lower surface are for purposes of illustration and first and second passages 128, 130 may be located at any position around second tube 104.

FIGS. 2A-2C show inner cannula 100 as it would be inserted into an outer tracheostomy tube 202, creating irrigating intraluminal suction inner cannula system 200. Components of FIGS. 2A-2C not specifically addressed below are the same as components described above in connection with FIGS. 1A-1E.

System 200 includes an outer tracheostomy tube 202, which represents either the patient's existing tracheostomy tube or one specifically designed for use with inner cannula 100. In embodiments, a specifically-designed outer tracheostomy tube 202 may fit with inner cannula 100 as part of a kit. For example, outer tracheostomy tube 202 may have indentations in its inner surface that engage with ridge 112 and improve the function of inner cannula 100. As depicted in FIGS. 2A, only a portion of outer tracheostomy tube 202 is shown. A portion of outer tracheostomy tube 202 is cutaway to show first tube 102 and the engagement between ridge 112 and an internal surface of outer tracheostomy tube 202. In addition, outer tracheostomy tube 202 would extend towards second tube 104 and provide a mechanism for engaging retaining clips 106. This mechanism could have several different forms and is omitted for clarity of illustration. FIG. 2B shows system 200 with a full outer tracheostomy tube 202.

The length of outer tracheostomy tube 202 is approximately equal to first tube 102 of inner cannula 100 as shown in FIG. 2B. The diameter of outer tracheostomy tube 202 is selected such that ridge 112 abuts the inner surface of outer tracheostomy tube 202 as shown at point 134 to form an airspace divided into regions 124 and 126. End 136 of first passage 128 in second tube 104 communicates with region 124 while end 138 of second passage 130 communicates with region 126 in second tube 104. As shown more clearly in FIGS. 1C and 1D, region 126 includes areas on opposite sides of first tube 102. In embodiments, ridge 112 may be formed on the inner aspect as part of outer tracheostomy tube 202 while still providing the regions or chambers discussed above. Alternatively, ridge 112 may be formed as part of both inner cannula 100 and outer tracheostomy tube 202 creating a single inseparable device.

In operation, inner cannula 100 may be used for suctioning and clearance of secretions in a patient's tracheostomy tube. Secretions build up on a regular basis and often require the use of intraluminal catheter based suctioning procedures, typically performed by another individual at present and often too viscous to be easily retrieved. Inner cannula 100 may fit into an existing tracheostomy tube or specifically designed accompanying tracheostomy tube. Once secured with retaining clips 106 for the patient's native tracheostomy tube (or accompanying tracheostomy tube), then either suction alone, or suction along with irrigation can be applied to remove secretions from the intraluminal space as well as the adjacent proximal end of the patient's tracheostomy tube. In embodiments, suction, or suction and irrigation, may also be applied to an extraluminal subglottic region. Irrigation may be performed with an irrigant solution, for example, saline. In embodiments, other solutions may be used, such as mucolytics, antibiotics, antifungals, steroids, or other medications. The irrigation combination with suction application also washes the inner lumen of the tracheostomy tube and suction chamber and therefore thins (decreases viscosity) the secretions to allow for easier suctioning and clearance of these secretions to prevent build-up and blockage, as well as to decrease the burden of pathogenic microbial colonization of the tube and airway tissues.

In embodiments, a method of using any of the cannulas disclosed herein is described in connection with FIGS. 3 and 4, which are best viewed together in the following description. For purposes of illustration, inner cannula 100 is depicted without outer tracheostomy tube 202. Inner cannula 100 fits into either a) the patient's existing tracheostomy tube or into b) an accompanying specifically designed tracheostomy tube—both a and b options represented by irrigating intraluminal suction inner cannula system 200 as disclosed herein. Once secured with retaining clips 106 for patient's native tracheostomy tube or accompanying specifically designed tracheostomy tube, the proximal end of suction line 302 is received by second passage 130. Suction line 302 may be a flexible plastic tubing terminating in fusion with a standard suction application tip 304. The proximal end of irrigant line 306 is received by first passage 128. Irrigant line 306 may be a flexible plastic tubing terminating in fusion with a with standard intravenous (IV) tubing connection 308, for example, a luer lock. In embodiments, suction line 302 and irrigation line 306 have a resting/failsafe closed position which prevent: a) loss of positive pressure (i.e., a leak) in the setting of mechanical ventilation, b) spontaneous flow of irrigant, and c) spontaneous application of suction to the device.

Figure 4:
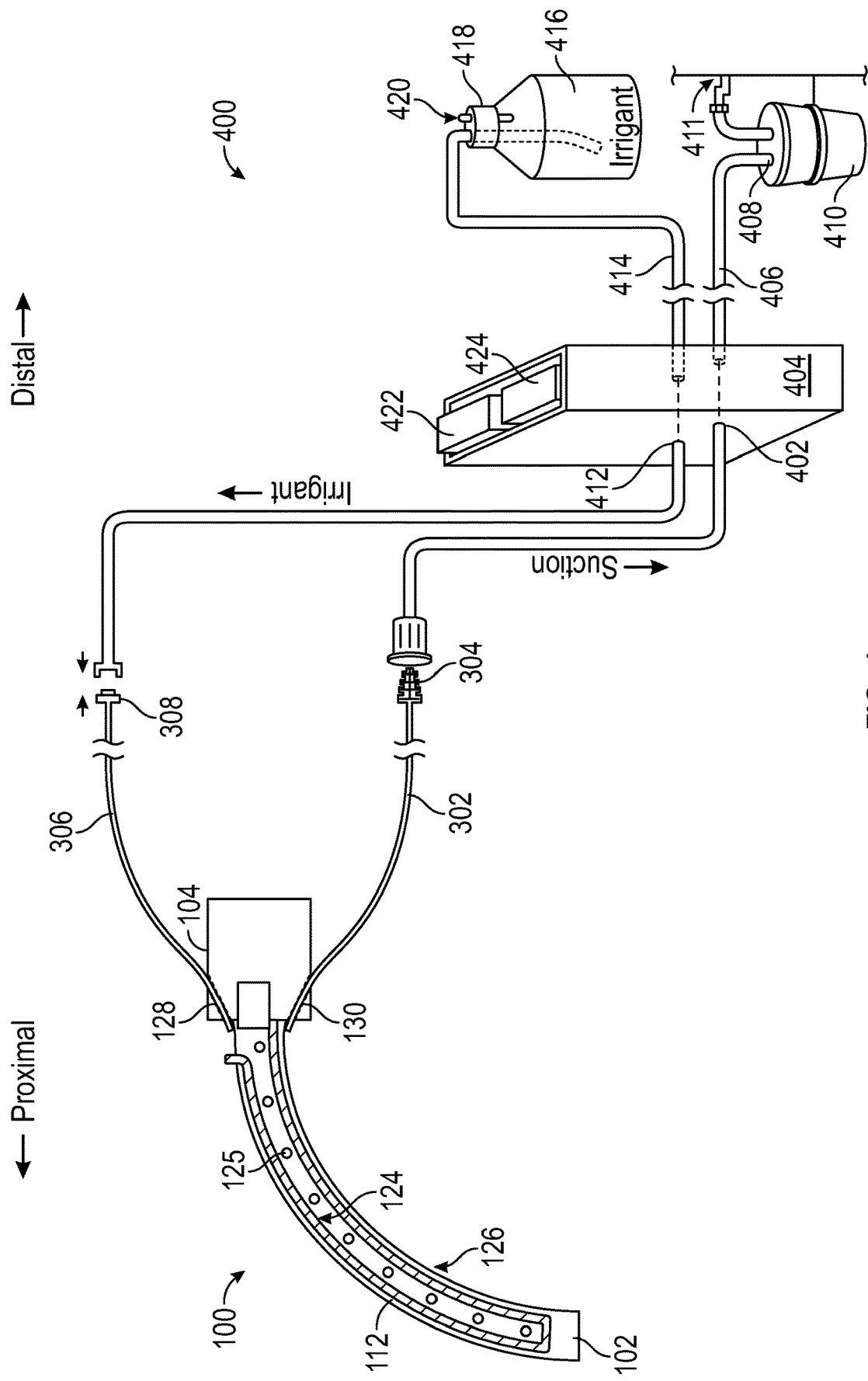
FIG. 4 is an irrigating intraluminal suction inner cannula system, in embodiments.

FIG. 4 shows irrigating intraluminal suction inner cannula system 200 connected with additional apparatus to form active use system 400. Active use system 400 is an example of system 200 in use. A distal end of suction line 302 is applied to suction line input 402 on actuating device 404. Suction line 406 distal to actuating device 404 is coupled to input 408 of vacuum source receptacle 410. Receptacle 410 may be connected to a continuous suction/negative pressure source such as, for example, a hospital wall-mount vacuum fitting or portable suction unit.

Similarly, irrigant line 306 from inner cannula 100 is coupled to the appropriate irrigant line input 412 on actuating device 404. Irrigant line 414 that is distal to the actuator device 404 is applied to irrigant bottle 416 through cap 418 with a straw to the bottom of irrigant bottle 416. A vent 420 on cap 418 may be opened for ease of use and facilitation of irrigant flow with less resistance. Irrigant bottle 416 must either be placed on the floor near the patient or kept at least one vertical foot (or other determined distance as to prevent gravity flow when actuating device is open) below the patient's tracheostomy tube at all times. In embodiments, irrigant bottle 416 may be, for example, a vent-option irrigant bottle or a hanging bag attached to a patient bed or independent stand.

Once all components of FIG. 4 are appropriately secured, actuating device 404 is controlled to perform an operation of either suction only, or a combination of suction and irrigation through the actuation of buttons 422 and 424. Suction-only actuation using button 424 will draw air and secretions from within the intraluminal space 132 of inner cannula 100, through the region 126 formed by ridge 112 between inner cannula 100 and the inner surface outer tracheostomy tube 202 (FIGS. 2A-2D), and out distally through lines 302 and 406 eventually ending in the vacuum source receptacle 410, thus clearing intraluminal secretions. Although actuating device 404 is described in connection with buttons, any mechanism for controlling the operation of actuating device 404 and active use system 400 to provide the functions described herein may be used. Additional buttons and functions may also be provided as part of actuating device 404 and active use system 400.

If both suction button 424 and irrigation button 422 are actuated at the same time, irrigant originating distally in irrigant bottle 416 will be drawn through lines 414 and 306 by negative pressure applied through suction lines 302 and 406. Irrigant will be drawn into region 124 formed by ridge 112 between inner cannula 100 and the inner surface of outer tracheostomy tube 202. Irrigant will enter the intraluminal space 132 of inner cannula 100 through holes 125, mix with intraluminal air and secretions, and then exit through slots 127 (FIGS. 1A-1D) into region 126. This flow of irrigant will thin secretions and rinse the intraluminal space 132 of inner cannula 100, and eventually end in the vacuum source receptacle 410.

Actuating device 404 may be designed in a number of ways, as long as it provides control buttons or other actuators and a connection between suction and irrigant lines from a tracheostomy cannula, and sources of irrigant and suction, respectively. In embodiments, actuating device 404 includes buttons 422 and 424, which are able to be moved/depressed into alignment. More or fewer buttons may be provided. An outer plastic housing of actuating device 404 is shown as including input 402 for has suction line 302 and an output on the opposite side for line 406 provide suction to inner cannula 100. Outer plastic housing of actuating device 404 also has an input 412 for irrigant line 306 and an output for irrigant line 414 on the opposite side which passes through cap 418 into standard irrigant bottle 416. These inputs and outputs may be provided at any convenient location on actuating device 404. Actuating device 404 functions such that only when button 424 is depressed are the lumens of the two lines 302 and 406 aligned to allow flow, otherwise preventing flow when the button 424 is not actuated. Likewise, only when button 422 is depressed are the lumens of lines 306 and 414 aligned to allow flow. In embodiments, actuating device 404 prevents the flow of irrigant without application of suction; however, it will accommodate use of suction only. Other actuating device mechanisms for connecting lines 302 and 306 with lines 406 and 414, respectively, are contemplated. Further, actuating device may be provided as a component of another medical device.

The patient is protected from irrigant-only flow into the intraluminal space 132 of inner cannula 100 by both actuating device 404 which prevents irrigant flow in the absence of suction, and by ensuring that the irrigant bottle 416 is kept at least one foot (twelve inches)—or other determined distance as to prevent spontaneous flow. In other words, irrigant bottle 416 as well as hanging bag or any apparatus for providing irrigant must be located below the vertical height of the tracheostomy tube at all times in the absence of any other mechanism to limit flow of irrigant. Other means of controlling the flow of irrigant are contemplated. For example, possibly via use of a variant of actuating device 404, irrigant may be actively pushed through the same flow pattern described previously, but done so by means of a pump, or pressurized irrigant canister, in a continuous or pulsating fashion, rather than simply drawn through solely by the negative pressure created by vacuum source 411. This pump could be placed either proximal or distal to the actuating device. In embodiments, the holes 125 in inner cannula 100 may include a one-way valve or pressure relief type valve, such as a simple slit or defect in the material in this region which remains closed at baseline and opens with increases in pressure in the irrigant line proximal to the actuating device.

In embodiments, active use system 400 may include additional safeguards against failure. In the event of failure of irrigation or suction, a flow sensor (not shown) would monitor if excessive or unexpected flow of irrigant is detected and provide an alarm, or other notification, or means of cessation. Excessive flow of irrigant may alternatively be immediately stopped by removal of the inner cannula. Valves, flow-limiters, and mechanical or electrical flow and pressure sensors are also contemplated.

In the event of malfunction, or for regular interval care, inner cannula 100 may be un-clipped, removed, discarded, and replaced with a new cannula. Conventional catheter-based intraluminal suctioning may be performed with or without inner cannula 100 in place. It is also notable that operation can be performed while connected to a ventilator/source of positive pressure, or not. Furthermore, operation can be performed with either a cuffed or uncuffed tube or with a fenestrated or non-fenestrated tracheostomy tube. Control of actuating device 404 may be performed by the patient, healthcare provider or caretaker. In embodiments, actuating device 404 may also be actuated by a mechanism designed to hold and apply actuation/depression of buttons 422 and 424 by means of an electronically controlled device either on-demand by patient, healthcare provider, caretaker, or on an automated schedule, or at points where certain monitoring input conditions are met and recognized by an electronic monitoring system. Irrigant bottle 416 may be replaced as it is depleted or as part of a set schedule. Furthermore, any component may be removed and replaced as part of a set schedule or as deemed necessary by patient, healthcare worker, caretaker, as indicated by an electronic monitoring system, or established protocol.

A variety of methods may be used to manufacture an irrigating intraluminal suction inner cannula system, in embodiments. For example, inner cannula 100 or system 200 may be created by mold extrusion or by thermally and/or chemically affixing solid plastic roll material onto the cannula to give its configuration of raised ridges. Holes 125 and slots 127 on first tube 102 may be created by mold extrusion or via heat, drilling, cutting, grinding, or otherwise subtracting material. First tube 102 may be thermally and/or chemically fused with rigid plastic second tube 104. Tubes 102 and 104 may also be manufactured as one piece. Irrigant/irrigation line 306 and suction line 302 may be thermally and/or chemically fused in place to the rigid plastic second tube 104. Additive methods, such as 3D printing, are also contemplated.

FIG. 5 is a flowchart illustrating a method 500 of using an irrigating intraluminal suction inner cannula system 200. Method 500 includes steps 506 and 508. In embodiments, method 500 also includes at least one of steps 502 and 504.

In step 502, inner cannula 100 is inserted into an outer tracheostomy tube 202 to create irrigating intraluminal suction inner cannula system 200. In an example of step 502, inner cannula 100 fits into an existing outer tracheostomy tube 202 or a specifically designed accompanying tracheostomy tube. Inner cannula 100 is secured with retaining clips 106 to patient's native tracheostomy tube 202 or accompanying tracheostomy tube.

In step 504, suction and irrigant lines are connected to inner cannula 100. In an example of step 504, suction line 302 is attached to second passage 130 in second tube 104. In embodiments, irrigant line 306 is attached to first passage 128 in second tube 104. In embodiments, one or both of suction line 302 and irrigant line 306 may be permanently attached, or fused, to second tube 104.

In step 506, suction and irrigant lines are connected to vacuum and irrigant sources through an actuating device. In an example of step 506, suction line 302 is connected through actuating device 404 and suction line 406 to vacuum source receptacle 410. Irrigant line 306 is connected through actuating device 404 and irrigant line 414 to irrigant bottle 416.

In step 508, actuating device 404 is used to perform suction alone, or suction along with irrigation of inner cannula 100 or system 200. In an example of step 508, button 424 on actuating device 404 may be pressed to connect suction line 302 with suction line 406 to remove secretions from the intraluminal space 132 of the patient's tracheostomy tube 202. In addition, irrigant button 422 may be pressed to combine irrigant/irrigation with suction to wash the intraluminal space 132 of the tracheostomy tube and region 126 by thinning the secretions to allow for easier suctioning and clearance within a closed system. Actuating device 404 may be controlled by the patient, hospital personal or other caregiver. In embodiments, actuating device 404 may be incorporated within a ventilator (not shown) and programmed to coordinate with the operation of the ventilator. Further, actuating device 404 may be used with an electronically controlled device to apply actuation/depression of actuator buttons (or other method). An additional example would be control via ocular control device or neural integrated device as used by immobile patients such as those with neurodegenerative or paralytic conditions (e.g., Amyotrophic Lateral Sclerosis—ALS, trauma, etc). In any of these embodiments, actuating device may be actuated either on-demand by patient, healthcare provider, caretaker, either on an automated schedule, or at points where certain monitoring input conditions are met and recognized by an electronic monitoring system. In embodiments, this would provide additional flexibility, decrease care-burden and resources, and minimize exposure of others to aerosolized particles.

Accumulation of oral cavity and pharyngeal secretions in the region above an inflated cuff of an outer tracheostomy tube can lead to micro aspiration of secretions into the lungs and has been associated with the development of ventilator assisted pneumonia (VAP.) For this reason, several additional embodiments are contemplated to incorporate extraluminal subglottic suction alone, or irrigation and suction combined, in this region while still incorporating the intraluminal irrigation and suction described herein. These embodiments are demonstrated in FIGS. 6A-6C. Additionally, an irrigating intraluminal suction inner cannula system as described herein may also be used with fenestrated outer tracheostomy tubes and additional embodiments are shown in FIGS. 6D-6E.

Figure 6A:
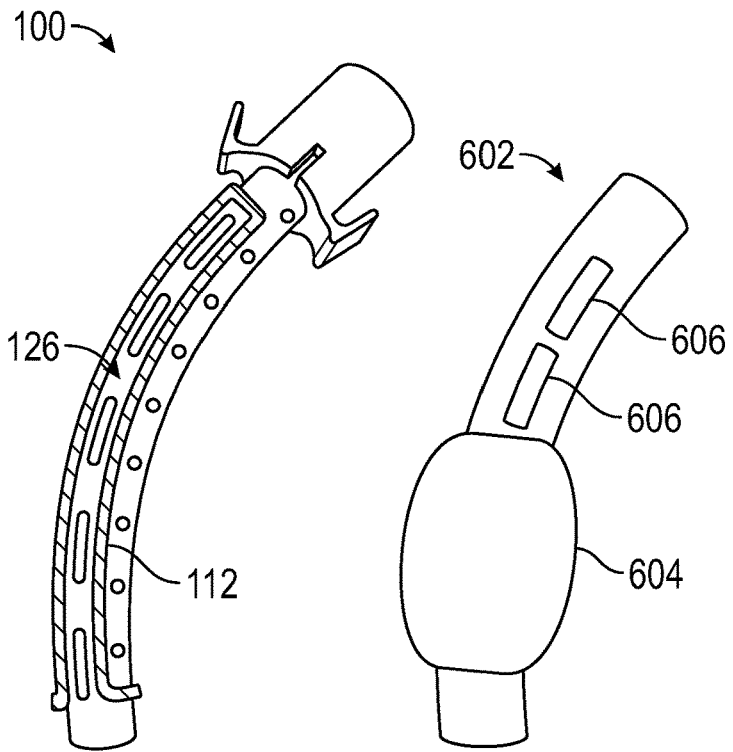
FIG. 6A is an oblique view of the irrigating intraluminal suction inner cannula system incorporating additional extraluminal subglottic suction capabilities and an accompanying cuffed outer tracheostomy tube, in embodiments.

FIG. 6A shows that inner cannula 100 as shown in FIGS. 1A-1D may be used with an outer tracheostomy tube with cuff 604 that is provided with additional suction holes 606. Single or multiple suction holes 606 are provided in cuffed outer tracheostomy tube 602 in the region of the subglottis, that is, above cuff 604 of a cuffed outer tracheostomy tube 602, and below the vocal cords, as shown in FIG. 7. Suction holes 606 may be positioned on the superior surface of cuffed outer tracheostomy tube 602 so as to overly corresponding region 126 of inner cannula 100 and thus, extend the intraluminal suction to the subglottic space. Additional suction holes 606 (not shown) may be provided on the opposite side of cuffed outer tracheostomy tube 602 aligning with the corresponding region 126. However, because the airspace of the lumen of the tracheostomy tube used for ventilation is contiguous with this extraluminal suction corridor created by this design, during positive pressure ventilation, an air leak into the subglottic space may exist, leading to discomfort or otherwise problematic side effects. Additionally, this may create a pathway for subglottic secretions to enter the intraluminal space and lead to aspiration of the secretions into the lower airways. Because of these shortcomings, two additional subglottic suction and subglottic irrigation and suction combination embodiments are contemplated and demonstrated in FIGS. 6B and 6C.

Figure 6B:
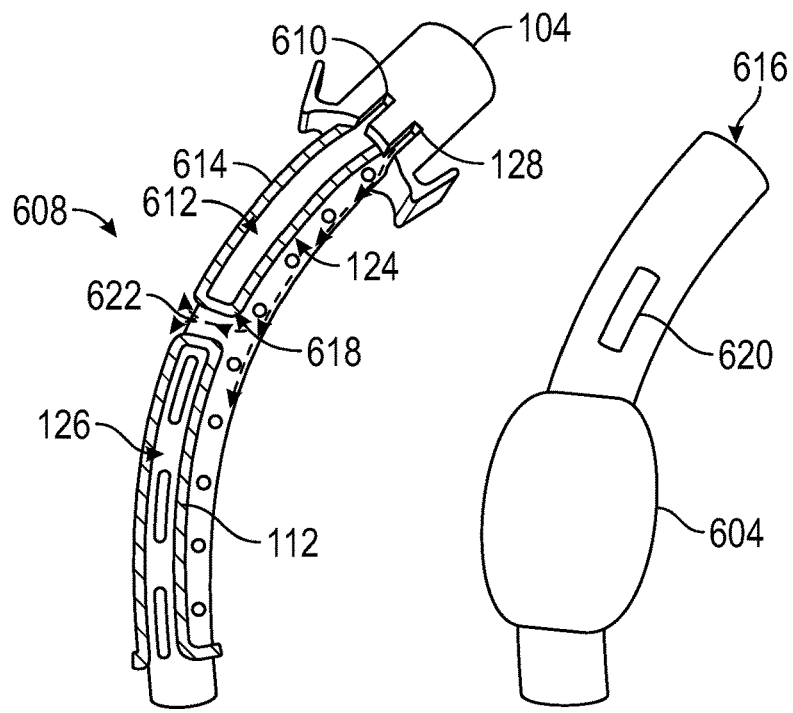
FIG. 6B is an oblique view of an alternate irrigating intraluminal suction inner cannula system incorporating additional extraluminal subglottic suction capabilities and accompanying cuffed outer tracheostomy tube, in embodiments.
Figure 7A:
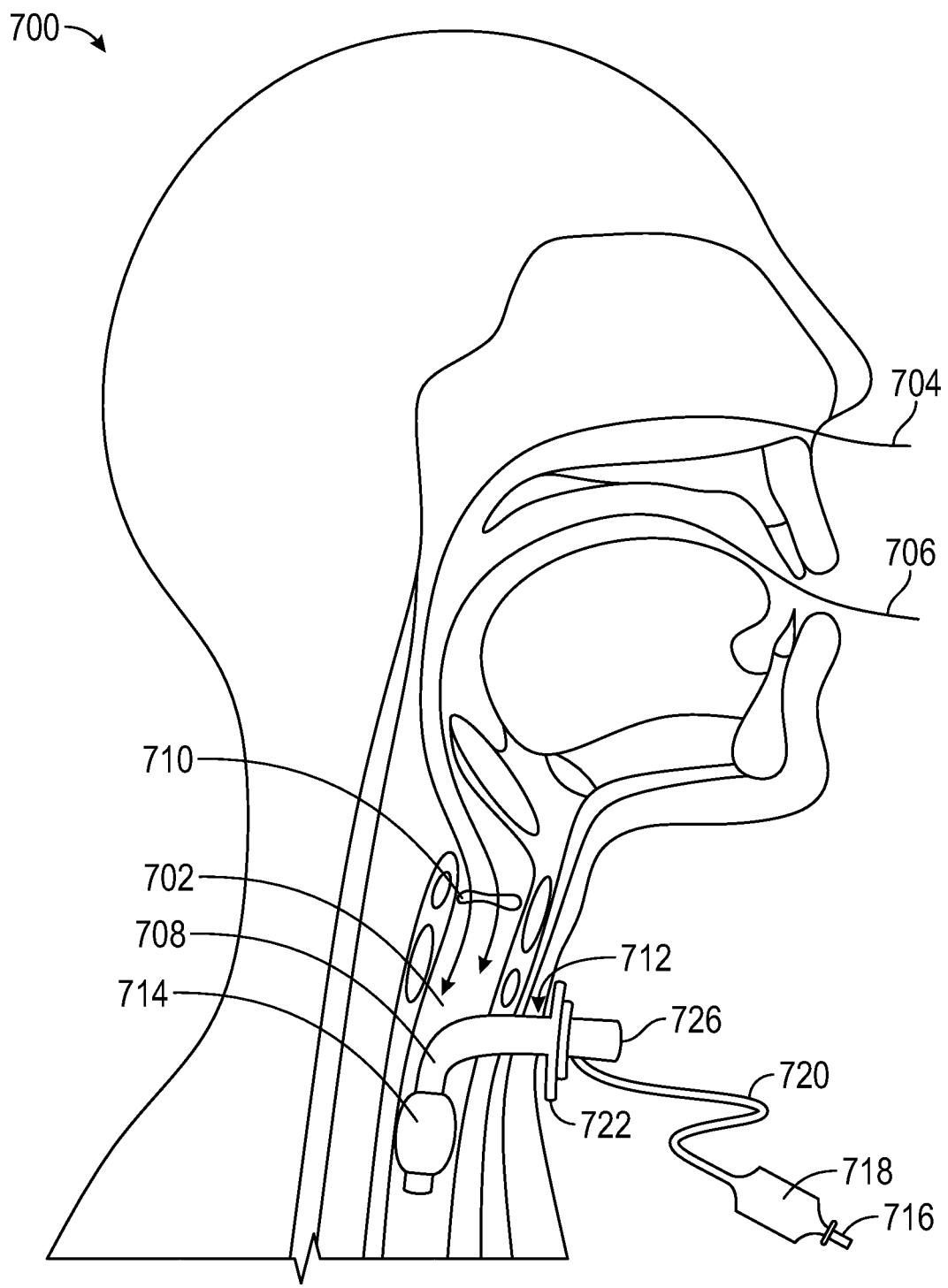
FIG. 7A is a cross-sectional side view diagram of a patient showing various types of prior art endotracheal tubes, in embodiments.
Figure 7B:
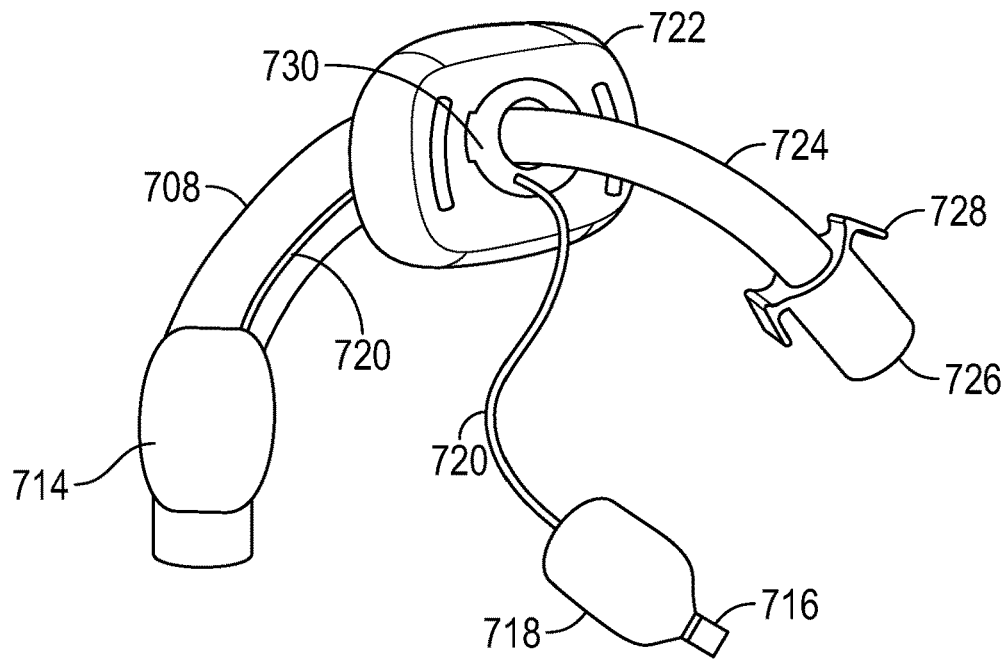
FIG. 7B is a perspective view of a prior art tracheostomy tube with an inner cannula, in embodiments.
Figure 7C:
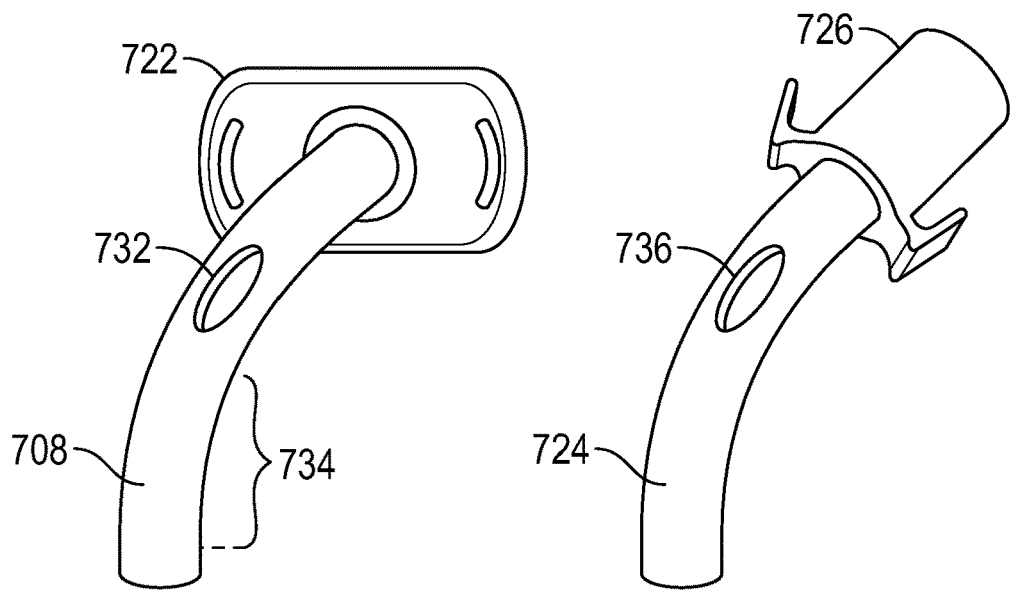
FIG. 7C is a perspective view of a prior art fenestrated tracheostomy tube and inner cannula, in embodiments.

In the embodiment of FIG. 6B, inner cannula 608 is a modified version of inner cannula 100. The following description refers to the accompanying drawings in which the same numbers in different drawings represent the same or similar elements unless otherwise represented. An additional passage 610 is created in second tube 104 for the attachment of a subglottic suction line (not shown). Passage 610 is an example of second passage 130. Subglottic suction occurs in region 612 created by ridge 614 on the inner cannula. Ridge 614 is similar to ridge 112 in that is creates a region, or chamber, between inner cannula 608 and outer tracheostomy tube 616. Ridge 614 starts at second tube 104, extends along the length of inner cannula 608 in the proximal direction, around the circumference of inner cannula 608 at point 618, then extends along the length of inner cannula 608 in the distal direction back to terminate at second tube 104. Ridge 112 is reconfigured as shown in FIG. 6B so that intraluminal suction, or irrigation and suction, may be provided with inner cannula 608 as described above.

Notably, there are no holes or slots region 612 as there are in region 126 and therefore, no communication between region 612 or extraluminal space outside outer tracheostomy tube 616 and the intraluminal space of inner cannula 608. Instead, a slot 620 is located in outer tracheostomy tube 616 so that it overlies region 612. By separate or similar control of an actuating device as described in connection with FIG. 4, when suction is applied through passage 610, secretions in the extraluminal subglottic space will be removed by suction. The embodiment of FIG. 6B only provides suction to the extraluminal subglottic space. First passage 128 in second tube 104 may be shifted from its position as shown in FIGS. 1A-1D, but still is contiguous with the region 124, and communicates with the opposite side of inner cannula 608 irrigation space via passthrough region 622. Therefore, a new path of suction is created, while still suppling suction and irrigation to all of the previously described holes in the inner cannula for purposes of intraluminal irrigation. A small area of superior intraluminal suction is sacrificed in this design.

Figure 6C:
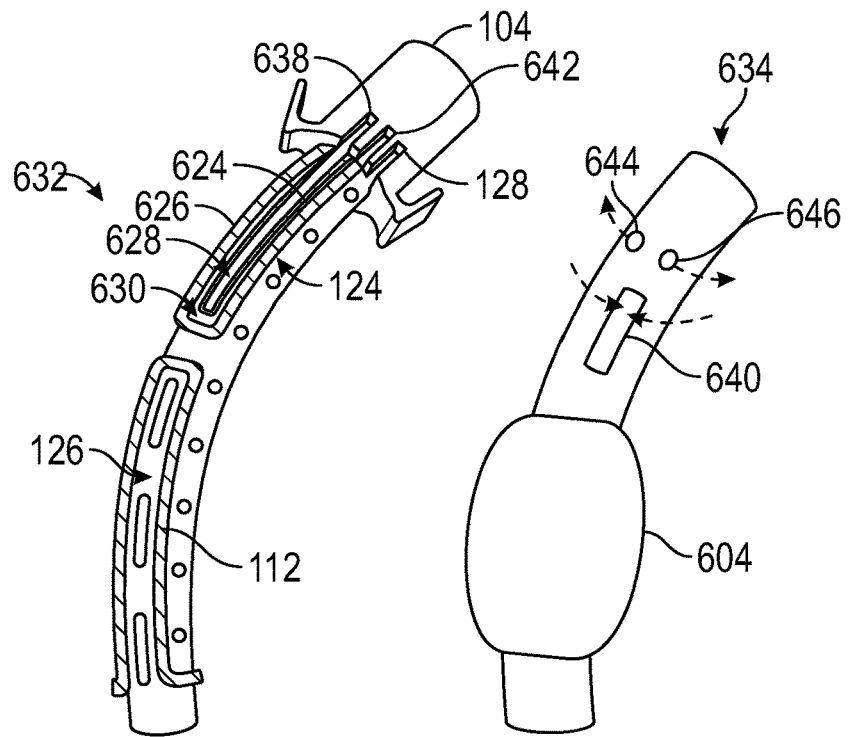
FIG. 6C is an oblique view of an irrigating intraluminal suction inner cannula system incorporating both irrigation and suction of the extraluminal subglottic region, with accompanying specifically designed cuffed outer tracheostomy tube, in embodiments.
Figure 6D:
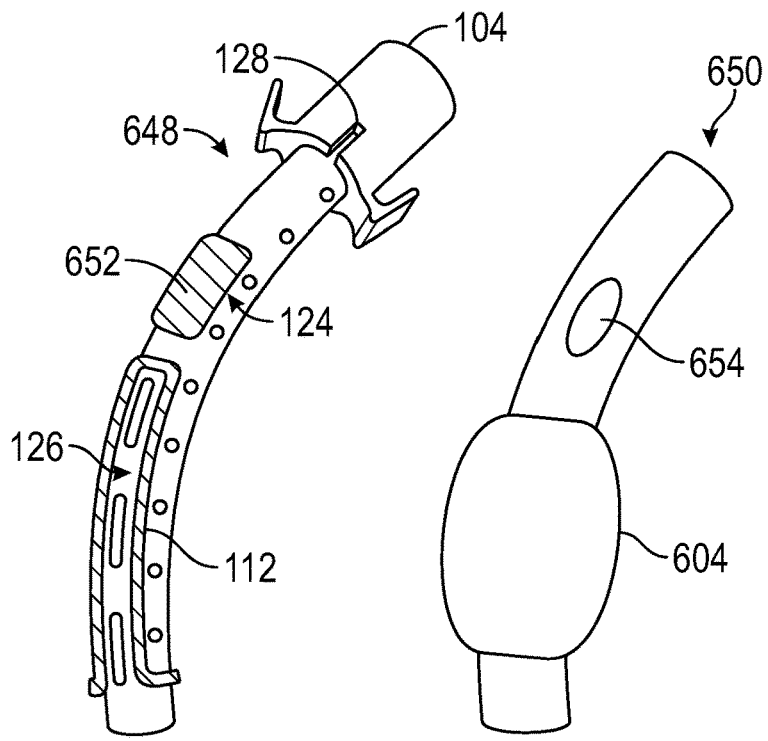
FIGS. 6D-6E are oblique views of an irrigating intraluminal suction inner cannula system for use with a fenestrated outer tracheotomy tube, in embodiments.
Figure 6E:
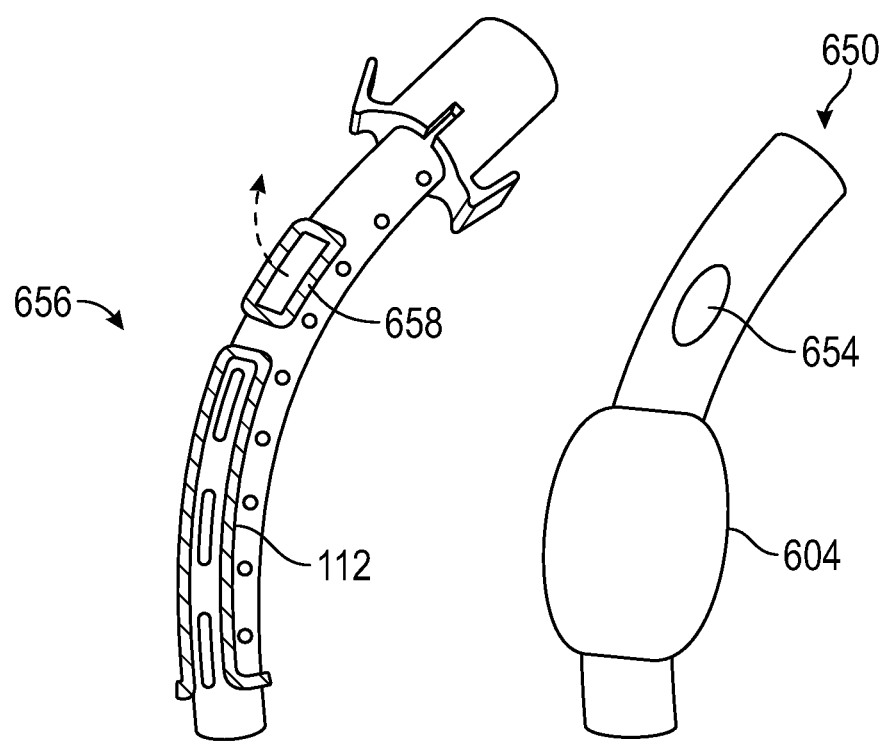

The embodiment of FIG. 6C incorporates both irrigation and suction to the extraluminal subglottic region, while again still achieving both intraluminal suction and irrigation. In this embodiment, first passage 128 in second tube 104 is again shifted to the side, but in the same manner as FIG. 6B, it remains contiguous with the region 124 via the same design of ridge 112 as shown in FIG. 6B. In FIG. 6C, ridge 614 is replaced with two parallel raised ridges including inner ridge 624 and outer ridge 626. Both inner ridge 624 and outer ridge 626 originate from second tube 104 and terminate again at second tube 104 as described above for ridge 614. This creates region 628 within inner ridge 624 and region 630 between inner ridge 624 and outer ridge 626. Like regions 124 and 126, regions 628 and 630 create a chamber between inner cannula 632 and outer tracheostomy tube 634. There are no holes or slots in either of regions 628 or 630 for communication with the intraluminal space of inner cannula 632. Passage 638 in second tube 104 is connected to a suction line (not shown) and contiguous with region 628 for providing suction to extraluminal subglottic region through opening 640 in outer tracheostomy tube 634. Passage 642 in second tube 104 is connected to an irrigation line (not shown) and contiguous with region 630 for providing irrigation to the extraluminal subglottic region through openings 644 and 646 in outer tracheostomy tube 634. As described above in connection with FIG. 4, an actuating device may cause the flow of irrigant from the supply/bottle 416 to be drawn through passage 642 to mix with secretions in the extraluminal subglottic space, then be drawn out through passage 638 to terminate in the same or separate suction canister or vacuum source receptacle 410. Other similar variations and relocations of the raised ridges and entry defects on inner cannula 632 and second tube 104 for subglottic suction are contemplated. Therefore, a new path of irrigant flow is created, while still suppling suction and irrigation to all of the previously described holes in the inner cannula for purposes of intraluminal irrigation.

FIG. 6D shows an embodiment of an irrigating intraluminal suction inner cannula 648 for use with a fenestrated outer tracheostomy tube 650. Fenestrated outer tracheostomy tube 650 may be desired in certain clinical scenarios to assess breathing and speaking capabilities. Inner cannula 648 is compatible with this type of outer tracheostomy tube design, or a specifically designed accompanying outer tracheostomy tube. Outer tracheostomy tube 650 may be either cuffed as shown or uncuffed. A raised, solid, block-like platform 652 is created on inner cannula 648 in the region of fenestration 654 of outer tracheostomy tube 650. Platform 652 is sized to abut the inner surface of outer tracheostomy tube 650. In this manner, the flow of air to and from the patient's airway to and from the subglottic region is blocked while irrigation and suction may still be provided using ridge 112 and regions 124 and 126 as described above. This blockage is sometimes desired.

Alternatively, flow of air to and from the patient's airway through the fenestration in an outer tracheostomy tube to and from the subglottic region is sometimes desired. To address this, an alternate embodiment shown in FIG. 6E is contemplated for use in fenestrated outer tracheostomy tubes that allows for this passage of air through fenestration 654. In FIG. 6E, irrigation intraluminal inner cannula 656 includes a roughly circular or ovoid raised ridge 658 in the same area and shape of overlying fenestration 654 on outer tracheostomy tube 650. In this embodiment, an accompanying opening within ridge 658 to the intraluminal space inside inner cannula 656 is intentional.

None of the embodiments in FIGS. 6A-6E compromise the irrigation or suction function of the intraluminal space described previously herein.

Active use system 400 decreases aerosolized airway particles because it is a closed system when used with a ventilator or a tracheostomy tube filter or nearly closed system when used without one. Either way this reduces respiratory aerosols and particles as well as the infection risk to others, an inherent risk of standard tracheostomy care.

In the event of malfunction, or for regular interval care, inner cannula 100 may be un-clipped, removed, discarded, and replaced with a new cannula without need for replacement of the outer tracheostomy tube. Conventional catheter-based intraluminal suctioning may be performed with or without inner cannula 100 in place.

A number of changes may be made to inner cannula 100 or system 200. For example, additional ridges may be used on first tube 102 to create further regions, or chambers/conduits for monitoring equipment and/or medication delivery. Ridge 112 on first tube 102 may be reconfigured for different patterns and subsequently different shapes of the irrigation and vacuum chambers, which may change their function. Similarly, passages in second tube 104 may be reconfigured for different patterns or shapes to permit functions of irrigation in suction chambers. Ridges 112 may allow for communication between the patient's airway to the external environment for the purpose(s) of airway monitoring devices and/or measurements or to deliver medications (droplet, aerosol, etc.).

Outer tracheostomy tube 202 may be configured with grooves or reliefs to help facilitate ease of insertion, different or improved function, or cleaning. The holes and/or slot locations, sizes, patterns, and shapes on first tube 102 may be reconfigured for varying flow of liquids and suction performance. In embodiments, inner cannula 100 may be lengthened (beyond tip of the outer tracheostomy tube 202), or shortened (to within the lumen of 202) to further enhance operational capabilities.

The lines for irrigation and suction may be altered to achieve the same suction by means of different locations on the hard plastic lumen of the invention, diameters, lengths, and connections. The shape and configurations of retaining clips, lumen and ridge sizes, lengths, and existing fenestrations could be applied to work with different existing tracheostomy tubes presently available, which vary in some or all of these regards.

An irrigating intraluminal suction inner cannula system may be used in other applications or areas of technology that requires the frequent replacement of inner lumens of a tube as a result of build-up of debris, secretions, or other matter; or, a similar system that does not have a replaceable inner lumen/cannula but could benefit from such to prevent clogging which results in damage or failure of the system as may presently be managed by intraluminal catheter-based suction. This could be in either medical or non-medical settings.

In healthcare environments, an irrigating intraluminal suction inner cannula system may be applied to other medical device/implant tubes which communicate with the external environment—such as oral endotracheal tubes, nasotracheal tubes, gastrostomy, colostomy, or nephrostomy tubes, intraperitoneal lumens, surgical drains, or other such applications in healthcare. The irrigating intraluminal suction inner cannula system could be used in many different settings, including both inpatient and ambulatory/portable settings.

This function of an irrigating intraluminal suction inner cannula system may be directed to or performed by a computer, machine, or other electronic means of monitoring and/or actuation of described functions.

An irrigating intraluminal suction inner cannula system, and the described, implied, or resultant use can produce compositions that may be of use or value. Monitoring of the secretions produced by its use may be of diagnostic use to healthcare providers. It may also provide for testing secretions for the presence of certain pathogens which can be detected or cultured, without introduction of additional instrumentation within the patient's airway, thus reducing risks from additional procedures.

The health outcomes data obtained by any regularly implemented or automated use of an irrigating intraluminal suction inner cannula system, with or without a machine or electronic control, may be a useful item in the creation of patient care protocols, reduction of patient morbidity and/or mortality, and development of patient care algorithms. Patient health outcomes may be improved as result of improved airway hygiene, which is a recognized standard of care in patients with tracheostomy tubes.

Functionality of the irrigating intraluminal suction inner cannula system requires only that it be appropriately secured and connected to a source of irrigant or other irrigation liquid, and a source of negative pressure (vacuum.) Safe and comfortable function may be enhanced by actuated control of irrigant and suction.

Changes may be made in the above methods and systems without departing from the scope hereof. It should thus be noted that the matter contained in the above description or shown in the accompanying drawings should be interpreted as illustrative and not in a limiting sense. Herein, and unless otherwise indicated: (a) the adjective "exemplary" means serving as an example, instance, or illustration, and (b) the phrase "in embodiments" is equivalent to the phrase "in certain embodiments," and does not refer to all embodiments. The following claims are intended to cover all generic and specific features described herein, as well as all statements of the scope of the present method and system, which, as a matter of language, might be said to fall therebetween.

Those skilled in the art could rearrange locations or sizes of fenestrations/configurations/ridges/volumes/shapes of the described irrigant and suction chambers, as alternate configurations are contemplated for various intended functions still within the scope of principles discussed herein.

The invention claimed is:

1. An inner cannula for use with a tracheostomy tube, comprising:
a first tube having a first diameter for insertion in the tracheostomy tube, a distal end and a proximal end, said first tube further comprising a plurality of holes between an intraluminal space of the first tube and an outer surface of the first tube, and a continuous ridge on the outer surface of the first tube, the continuous ridge having a height that abuts an inner lumen of the tracheostomy tube, wherein the continuous ridge extends at least along a first length of the first tube in a proximal direction, around a circumference of the first tube, and along a second length of the first tube in the distal direction, the continuous ridge dividing an airspace surrounding the outer surface into a plurality of separate regions including at least a first region and a second region; and
a second tube fused to a distal end of the first tube and having a second diameter larger than the first diameter, the said second tube comprising a first passage between an outer surface of the second tube and the first region and a second passage between the outer surface of the second tube and the second region.

2. The inner cannula of claim 1, said second tube further comprising retaining clips for attaching the inner cannula to the tracheostomy tube.

3. The inner cannula of claim 1, wherein the first passage is connectable to a line coupled to a source of irrigant.

4. The inner cannula of claim 1, wherein the second passage is connected to a line coupled to a vacuum source.

5. An irrigating intraluminal suction inner cannula system comprising:
an outer tracheostomy tube;
an inner cannula positioned inside the outer tracheostomy tube, comprising:
a first tube having a first diameter for insertion in the tracheostomy tube, a distal end and a proximal end, said first tube further comprising a plurality of holes between an intraluminal space of the first tube and an outer surface of the first tube, and a continuous ridge on the outer surface of the first tube, the continuous ridge having a height that abuts an inner lumen of the tracheostomy tube, wherein the continuous ridge extends at least along a first length of the first tube in a proximal direction, around a circumference of the first tube, and along a second length of the first tube in the distal direction, the continuous ridge dividing an airspace surrounding the outer surface into a plurality of separate regions including at least a first region and a second region; and
a second tube fused to a distal end of the first tube and having a second diameter larger than the first diameter, the said second tube comprising a first passage between an outer surface of the second tube and the first region and a second passage between the outer surface of the second tube and the second region; and
an irrigant line attached to the first passage in the second tube and in communication with the first region;
a suction line attached to the second passage in the second tube and in communication with the second region; and
an actuating device coupled between the irrigant line and a source of irrigant and coupled between the suction line and a vacuum source, said actuating device controllably connecting the irrigant line to the source of irrigant and the suction line to the vacuum source.

6. The cannula system of claim 5, wherein the outer tracheostomy tube further comprises indentations on an inner surface in the same pattern as the continuous ridge such that the continuous ridge engages with the indentations when the inner cannula is inserted into the outer tracheostomy tube.

7. The cannula system of claim 5, wherein the actuating device may be coupled between only the suction line and the inner cannula.

8. The cannula system of claim 5, wherein the actuating device may be incorporated within a ventilator.

9. The cannula system of claim 5, wherein the source of irrigant is positioned at a distance below a vertical height of the inner cannula to prevent spontaneous flow.

10. The cannula system of claim 9, further comprising a flow sensor for monitoring excessive or unexpected flow of irrigant or suction.

11. The cannula system of claim 10, further comprising valves, flow-limiters, mechanical flow and pressure sensors, or electrical flow and pressure sensors.

12. The cannula system of claim 11, further comprising an alarm or notification when excessive or unexpected flow of irrigant or suction is detected.

13. The cannula system of claim 5, wherein the second tube further comprises retaining clips for attaching the second tube to the outer tracheostomy tube.

14. The cannula system of claim 5, wherein the outer tracheostomy tube and the inner cannula form a single device.

15. The cannula system of claim 5, wherein the outer tracheostomy tube is a cuffed or uncuffed tracheostomy tube.

16. The cannula system of claim 5, wherein the outer tracheostomy tube is a fenestrated or non-fenestrated tracheostomy tube.

17. An irrigating intraluminal suction and extraluminal suction inner cannula system comprising:
   an outer tracheostomy tube comprising one or more openings along its length;
   an inner cannula positioned inside the outer tracheostomy tube, comprising:
      a first tube having a first diameter for insertion in the outer tracheostomy tube, a distal end and a proximal end, said first tube further comprising a plurality of holes between an intraluminal space of the first tube and an outer surface of the first tube, and a first continuous ridge and a second continuous ridge on the outer surface of the first tube having a height that abuts an inner lumen of the tracheostomy tube, wherein the first continuous ridge extends at least along a first length of the first tube in a proximal direction, around a circumference of the first tube, and along a second length of the first tube in the distal direction, the continuous ridge dividing an airspace surrounding the outer surface into a plurality of separate regions including at least a first irrigant region and a first suction region, and wherein the second continuous ridge extends along the length of the first tube in the proximal direction, around the circumference of inner cannula, then extends along the length of the first tube in the distal direction forming a second suction region aligned with the one or more openings in the outer tracheostomy tube; and
   a second tube fused to a distal end of the first tube and having a second diameter larger than the first diameter; and
   an irrigant line attached to an irrigant passage in the second tube and in communication with an airspace formed between the outer surface of the first tube and an inner surface of the outer tracheostomy tube in the irrigant region;
   a first suction line attached to a first suction passage in the second tube and in communication with an airspace formed between the outer surface of the first tube and an inner surface of the outer tracheostomy tube in the first suction region;
   a second suction line attached to a second suction passage in the second tube and in communication with an airspace formed between the outer surface of the first tube an inner surface of the outer tracheostomy tube in the second suction region; and
   an actuating device coupled between the irrigant line and a source of irrigant and coupled between the first and second suction lines and a vacuum source, said actuating device controllably connecting the irrigant line to the source of irrigant and the first and second suction lines to the vacuum source.

18. A method of cleansing an intraluminal space of a tracheostomy system comprising an outer tracheostomy tube and an inner cannula inserted in the outer tracheostomy tube using the irrigating intraluminal suction inner cannula system of claim 5.

19. A method of cleansing an extraluminal/subglottic space of a tracheostomy system comprising an outer tracheostomy tube and an inner cannula inserted in the outer tracheostomy tube using the irrigating intraluminal suction and extraluminal suction inner cannula system of claim 17.

20. A method of cleansing a tracheostomy tube comprising an outer tracheostomy tube and the inner cannula of claim 1, the method comprising:
   attaching a suction line to the second passage of inner cannula so that it is in communication with the second region;
   attaching an actuating device between the suction line and a vacuum source, said actuating device controllably connecting the suction line to the vacuum source; and
   controlling the actuating device to apply suction to a lumen of the inner canula through the plurality of holes, in the second region.

21. The method of claim 20, further comprising:
   attaching an irrigant line to the first passage of the inner cannula so that it is in communication with the first region;
   attaching the actuating device between the irrigant line and a source of irrigant, said actuating device controllably connecting the irrigant line to the source of irrigant; and
   controlling the actuating device to provide irrigant to the lumen of the inner canula through the plurality of holes in the first region.

* * * * *